(12) United States Patent
Cushman

(10) Patent No.: US 6,302,859 B1
(45) Date of Patent: Oct. 16, 2001

(54) TRACTION DEVICE

(76) Inventor: Ralph B. Cushman, 4600 Timberlux Cir., Anchorage, AK (US) 99516

( * ) Notice: Subject to any disclaimer, the term of this patent is extended or adjusted under 35 U.S.C. 154(b) by 0 days.

(21) Appl. No.: 09/542,628

(22) Filed: Apr. 4, 2000

(51) Int. Cl.$^7$ .................................................. A61F 5/00
(52) U.S. Cl. ................................ 602/32; 602/33; 602/35; 602/36
(58) Field of Search ........................................ 602/32–40

(56) References Cited

U.S. PATENT DOCUMENTS

| | | | |
|---|---|---|---|
| 3,134,379 | * | 5/1964 | Nightingale ............................. 602/32 |
| 5,115,802 | * | 5/1992 | Dyer ....................................... 602/36 |
| 5,868,694 | * | 2/1999 | Marlow ................................... 602/32 |
| 6,007,507 | * | 12/1999 | Ledany ................................... 602/32 |
| 6,123,680 | * | 9/2000 | Brummer ................................. 602/35 |

OTHER PUBLICATIONS

Homestretch, portable, pneumatic–powered lumbar traction 1999<http"//www.glaciercross.com/homestretch.html.

The VAX–D Network–VAX–D; "The Non–Surgical Solution to Low Back Pain"<http://www.vaxd.net/>.

* cited by examiner

Primary Examiner—Michael A. Brown
(74) Attorney, Agent, or Firm—Brown & Michaels, PC

(57) ABSTRACT

The present invention utilizes a user's arm strength opposed by large stretch bands attached to the harness to achieve 100% of the traction force or "pull-weight." The principal components of the device are an anchoring system, such as a frame, and a harness, which are used simultaneously as part of a single system. The user lies upon a body support atop the frame and uses his/her arm strength to slide forward by pulling with his/her hands against a harness fastened around the user's waist. The user accomplishes the sliding forward by pulling on handles attached to the top of the frame, while the harness is attached to the bottom of the frame. The effect is distraction of the lower spine. The unique mode of action of the device utilizes the user's own arm strength to achieve a completely variable traction force. The user is in complete control of the amount of traction force to be delivered at all times without any dependence upon electricity to generate force. It provides instantly variable traction force over a wide range of pull-weights, even into the higher weight ranges.

28 Claims, 3 Drawing Sheets

TRACTION DEVICE

BACKGROUND OF THE INVENTION

1. Field of the Invention

The invention pertains to the field of therapeutic devices using traction force. More particularly, the invention pertains to a traction device that utilizes the user's arm strength to achieve the traction force and body inertia to maintain the traction.

2. Description of Related Art

Many people have serious, chronic pain in their lower back caused by degenerative disc disease, spondylosis, spondylolisthesis, spinal stenosis, sciatica, herniated discs, bulged discs or ruptured discs. Often, surgery is the only option or, even worse, there is no way to alleviate the pain.

One treatment for pain is the use of traction devices. An example of this type of device is the VAX-D™ traction device (http://www.vax-d.net). This device is a powered traction system utilizing an electric winch. Its use is administered in a clinic. The VAX-D traction force is not controlled by the user but by a computer that regulates the winch. The user holds onto two handles and submits to the pre-programmed traction force of the machine.

Another method of achieving variable distraction of the lower spine is that used by the "Homestretch" device (http://www.glaciercross.com/homestretch.html). The "Homestretch" device delivers up to 180 pounds of traction (60 PSI) provided by a hand-held air pressure pump. The pump includes a gauge and a release valve for intermittent traction. Similar to the VAX-D system, the "Homestretch" system is a powered device.

Other traction devices utilize powered winches or suspended weights to achieve the traction force. Many traction devices employ a harness, but connect it to a suspended weight in order to achieve traction force. These devices do not provide user-controlled, variable traction, nor can traction force in the upper ranges be achieved.

There are also numerous "inversion" traction devices, all involving hanging the user upside down, held either by the feet, legs or hips, and using the weight of the upper body, for achieving distraction of the lower spine. These types of devices only supply fixed traction.

Currently there is no non-powered home traction device, and very few clinical traction devices, which deliver true variable traction. Due to the fact that the pull-weight can not be changed easily on these devices, a user typically gets too much pull-weight at the beginning of a session, which can easily cause cramping and be very painful, and then not enough late in a traction session. There is a need in the art for a user-controllable, non-powered traction device for home use.

SUMMARY OF THE INVENTION

The traction device is a simple, inexpensive, safe, and effective system made up of several components. The device is used for self-administering variable pull-weight traction to the lower back ("distraction of the lumbar spine"). Its principal components are an anchoring system, such as a frame, a harness and a body support, which are used simultaneously as part of a single system. The user lies upon the body support atop the frame and uses his/her arm strength to slide forward by pulling with the hands, against a harness fastened around the user's waist. The user accomplishes the sliding forward by pulling on handles attached to the top of the frame, while the harness is attached to the bottom of the frame, with the effect being distraction of the lower spine. The invention utilizes the user's arm strength opposed by large stretch bands attached to the harness to achieve 100% of the traction force or "pull-weight."

DETAILED DESCRIPTION OF THE INVENTION

Traction is hardly a new concept in spine therapy. It works to relieve lumbar disc pain by decompressing the vertebrae, putting them back where they used to be and pulling the bulged disc or out-of-place vertebrae away from the impinged nerve. But just as athletes in excellent condition have to stretch and warm-up their muscles before stressing them, a user needs to slowly and carefully ease their back into traction. With the traction device of the present invention, it is easy and convenient to achieve this.

The present invention utilizes the user's arm strength opposed by large stretch bands attached to the harness to achieve 100% of the traction force or "pull-weight." The unique mode of action of the device utilizes the user's own arm strength to achieve a completely variable traction force. The traction force varies from zero to approximately 100 lbs. or more traction force for adult males with normal arm strength, and from zero to approximately 50 lbs. or more for other individuals.

The user is in complete control of the amount of traction force to be delivered at all times without any dependence upon electricity to generate force. It provides instantly variable traction force over a wide range of pull-weights, even into the higher weight ranges. In contrast, prior art inversion devices only supplied fixed traction.

The invention provides the comfort of face-down orientation. Body position is important with spinal traction. With the traction device, the user is lying face-down, so that the user relaxes during the traction session, his/her spine falls into what is, for most people, a much more comfortable posture than that which occurs in any other traction position.

The design of the traction device allows the spine to be pulled at the best angle. This is because the device pulls the vertebrae apart from the waist, pulling the entire pelvis down rather than pulling by the legs, as some of the inversion devices do, and as happens if a user hangs from a bar or uses something similar.

Figure 1:
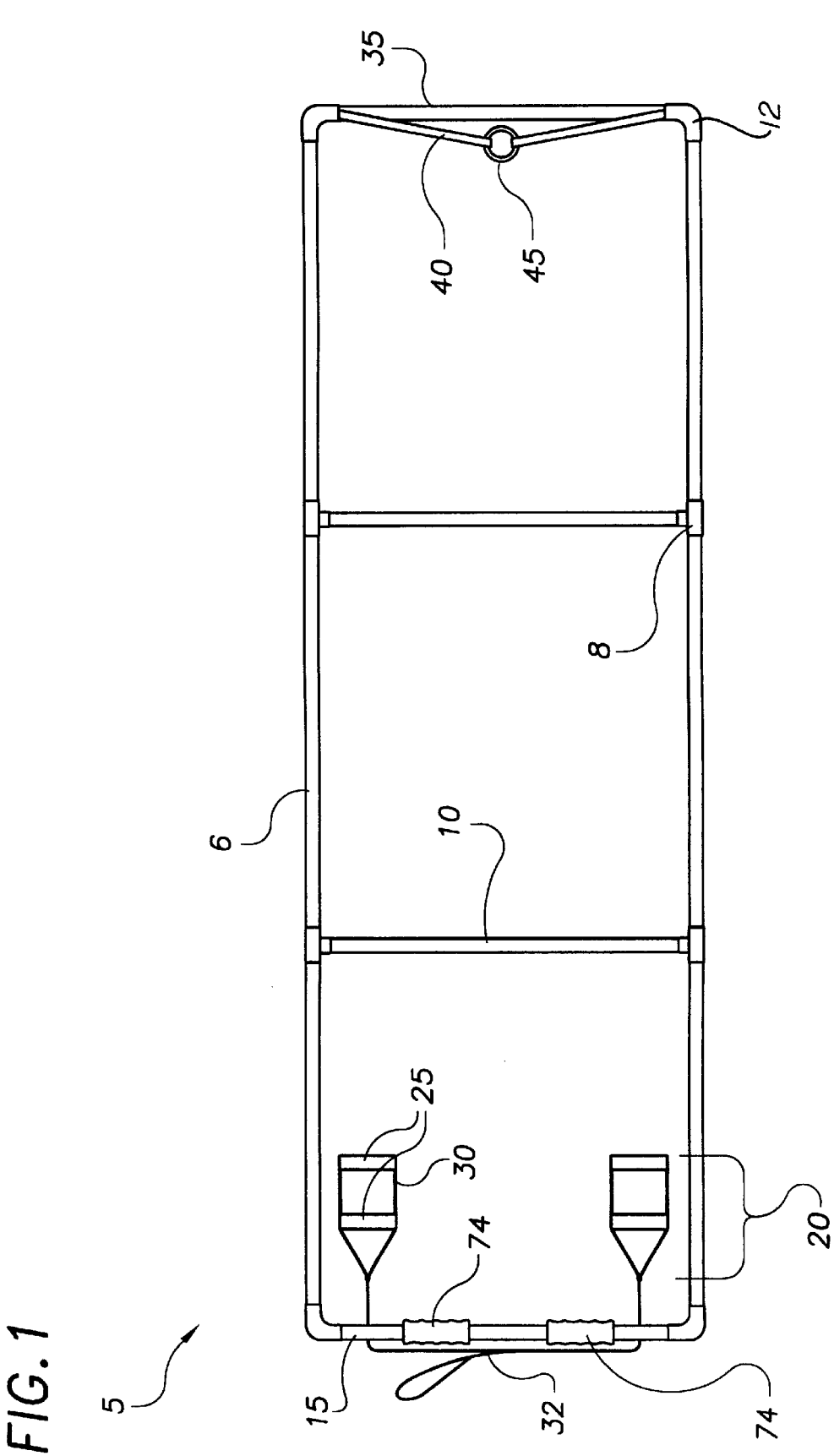
FIG. 1 shows an aerial view of a frame for the traction device in an embodiment of the present invention.

A frame (5) shown in FIG. 1 is a preferred anchoring system for the handles (20) of the traction device. The frame (5) is preferably constructed out of pieces of 1" PVC pipe. In a preferred embodiment, ten pieces of 1" PVC pipe (6), each approximately 32" long, are connected together with the PVC tee (8) and elbow (12) fittings customarily used for joining this type of pipe when it is used in waterline systems. This makes for a sturdy, inexpensive, lightweight frame (5) which is easily assembled and disassembled. Alternative materials for constructing the frame (5) include aluminum, steel, wood or any other rigid material. The frame (5) is preferably supported by any carpeted floor while the traction device is in use.

The frame (5) is preferably rectangular in shape, with dimensions sufficiently large so that an average user can lie comfortably on the traction device. For example, dimensions of approximately 8 feet long and 3 feet wide (34"×100") should be sufficient for all but the tallest and largest users. The frame preferably includes at least two cross-supports (10) to provide rigidity and reduce bending of the frame in use.

The user's hands grip the traction device at or near the top (15) of the frame (5), the "top" being defined as the end of the frame closest to the user's head. In the preferred embodiment, this is done through two handles (20), preferably including one or more grips (25), and a rope (30) attaching the handle (20) to the top (15) of the frame (5). The length of the rope (30) is variable (32) to suit the dimensions of the user. Alternatively, a single wider handle could be used, crossing between the two ropes (30) like a trapeze handle, or the grip (25) could be made wide enough for both the user's hands to grip, and only one of the two handles (20) would then be needed. In another embodiment, rubber or plastic handgrips (74) could be placed directly on the upper rail (15) of the frame (5), and the variations in the user's height could be accommodated by adjusting the length of the tensioning cable (70) or the side rails (6) of the frame.

At the bottom (35) of the frame (5) are stretch bands (40). These stretch bands (40) are preferably of an elastic material such as rubber or elastic straps commonly known as "bungee cords", or alternatively could be made of springs. There are preferably 2, 4, or 6 of these stretch bands (40) found on the traction device. Steel "S" hooks are preferably inserted into holes drilled into the frame to permanently attach the stretch bands (40) to the frame (5). There is a central attachment point (45) through which each of the stretch bands (40) passes or is attached. The harness (50) (described below and shown in FIGS. 2A–2C) worn by the user connects to the central attachment point (45).

The stretch bands (40) are an important component of the traction device for two reasons. First, their use permits very precise control and instant adjustment (increase or decrease) of the traction force. This control is much greater than in prior art devices, where the harness (50) was simply connected directly to a suspended weight. Second, the stretch bands (40) prevent exhaustion of the user's arm during traction, as once the user has pulled his/her body forward, he or she can greatly reduce the pull being applied by his/her arms, or even cease pulling altogether, and yet remain under considerable traction. Without the stretch bands (40), the traction force falls immediately to near zero when the user stops pulling with his/her arms.

The frame provides an "anchor" at the user's head to which the handles (20) are attached, and also provides an anchor at the user's feet to which the harness (50) is attached, so that when the user pulls on the handles (20) he or she pulls against the harness (50) around his/her waist, with the result being a stretching or "distraction" of the lower spine. In an alternative embodiment, the entire frame (5) is replaced with some other anchoring system. For example, the handles (20) are attached to a wall or other anchor, and the stretch bands (40) are attached to an opposing wall or another anchor.

Figure 2:
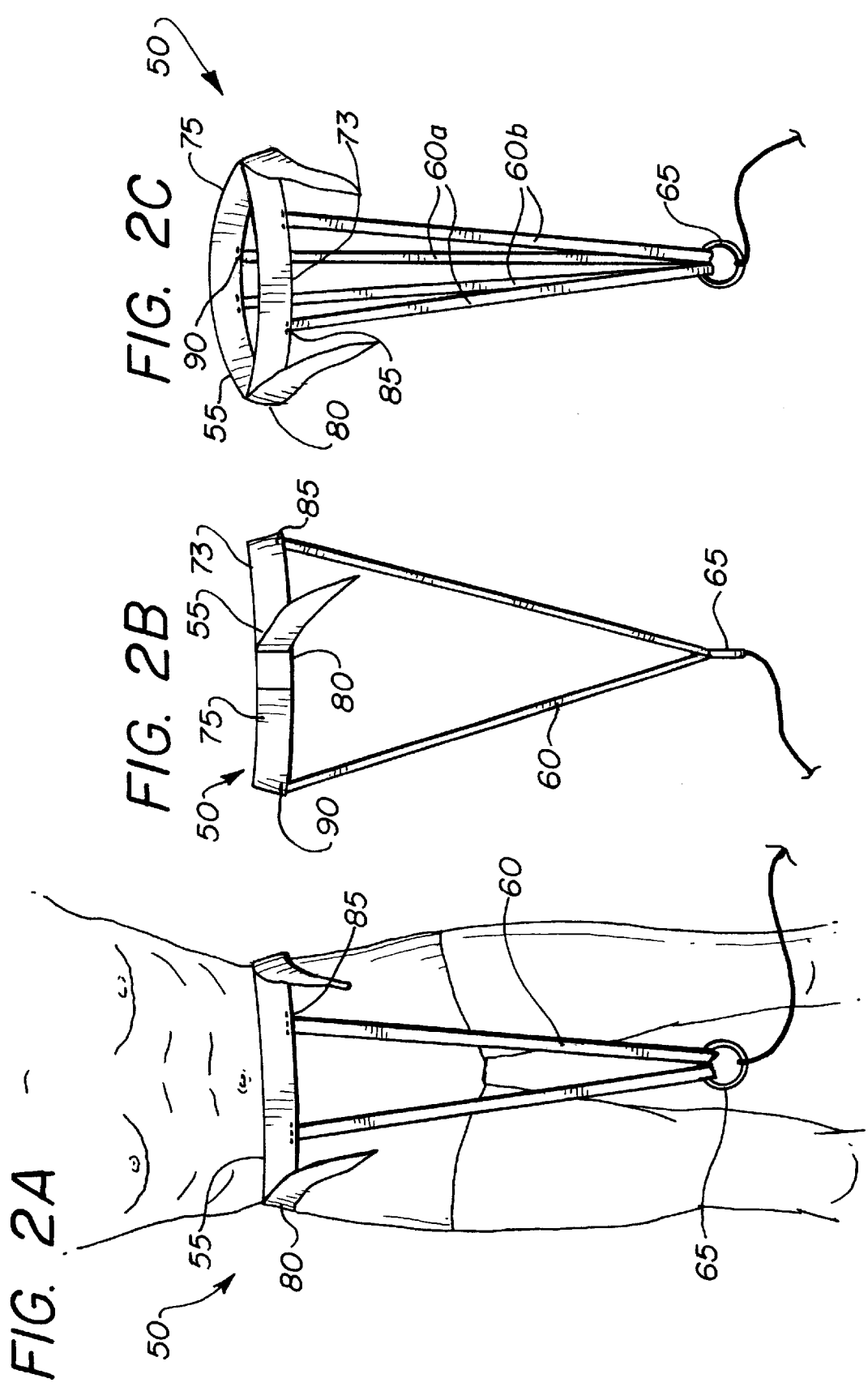
FIG. 2A shows a front, two-dimensional view of a harness as worn by a user in an embodiment of the present invention.
FIG. 2B shows a side, two-dimensional view of the harness in FIG. 2A.
FIG. 2C shows a front, three-dimensional view of the harness in FIG. 2A.

Referring also to FIGS. 2A–2C, the harness (50) has a waistband (55), at least two downstraps (60), and a sliding ring (65). The waistband (55) and the downstraps (60) are preferably constructed of nylon strapping material, or "webbing". The preferred width for the waistband (55) is approximately 2", and 1" for the downstraps (60). The downstraps (60) pass through the sliding ring (65) which connects via a tensioning cable (70) to the central attachment point (45) attached to the stretch bands as shown in FIG. 3.

The waistband (55) of the harness (50) preferably has a front section (73) and a rear section (75) which connect together via two buckles (80) (one on each side) to form a single waistband (55) around the user. Each of the two downstraps (60) connects, preferably by sewn thread, to the waistband (55) in the front section (73) and in the rear section (75). One downstrap (60a) connects to the left-side front section and to the right-side rear section of the waistband (55), and the other downstrap (60b) connects to the right-side front section and to the left-side rear section of the waistband (55). The design of the waistband (55) is such that, when properly adjusted, the two front downstrap connection points (85) are centered on the user's torso, approximately 6"–8" apart, and the two rear downstrap connection points (90) are likewise centered, the same distance apart.

The (equal) length of the downstraps (60) is such that when the user puts the harness (50) on and fastens the waistband (55) around his/her waist just above the hips, the sliding ring (65) through which the downstraps (60) pass is between the user's knees when the tensioning cable (70) is taut. The sliding ring (65) is preferably made of steel so that when traction force is applied, the sliding ring (65) slides and finds its point of natural equilibrium, causing equal pull on all four downstrap connection points (80 and 85).

Figure 3:
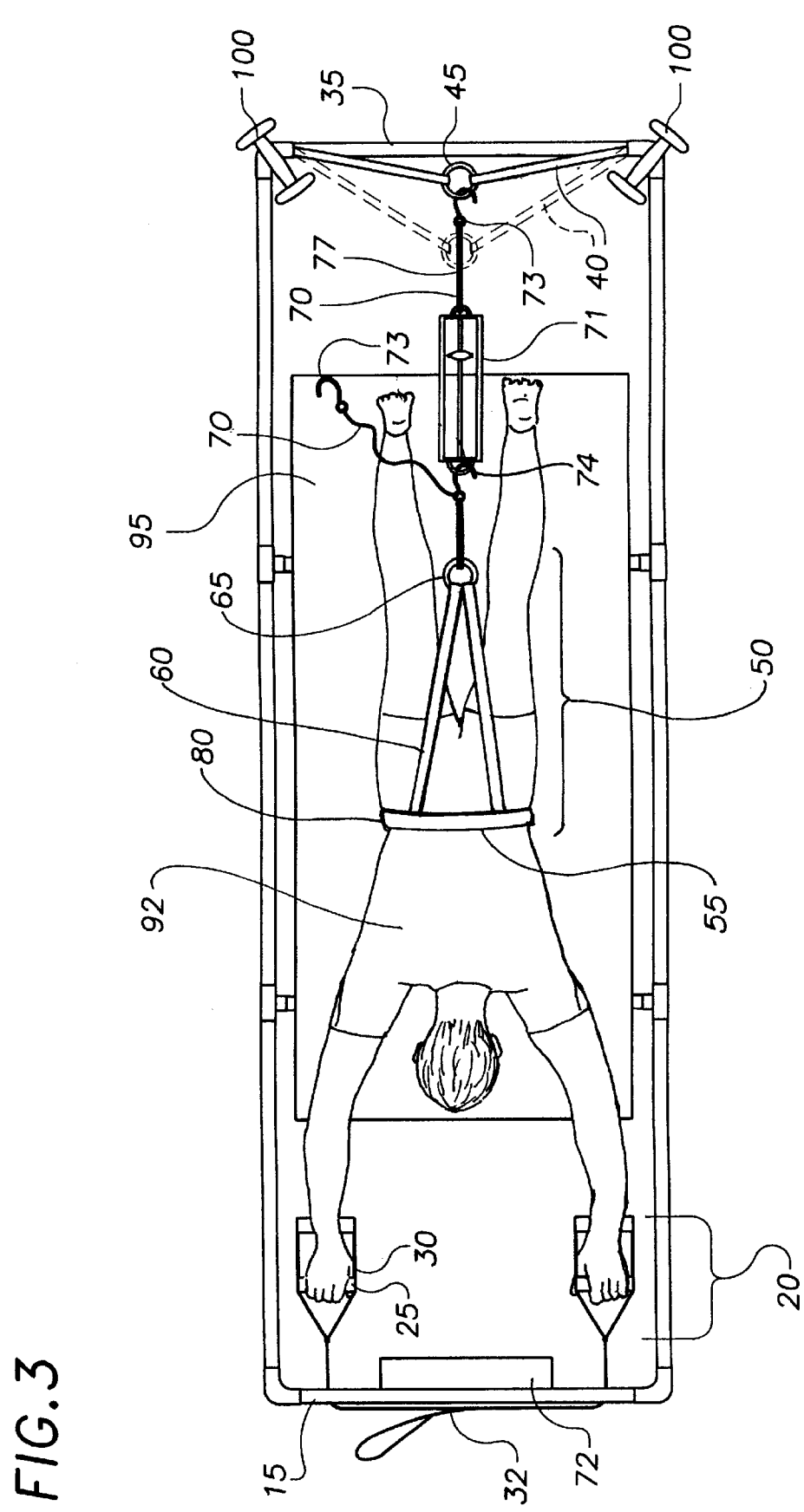
FIG. 3 shows an aerial view of the traction device of the present invention as it is being used by an individual.

Referring also to FIG. 3, attached to the sliding ring (65) on the downstraps (60) is a tensioning cable (70). The tensioning cable (70) is preferably a harness rope, wire, chain or webbing, with or without an in-line scale (71)(such as a spring scale of approximately 100 lb. capacity), depending on whether the user (92) desires measured or unmeasured traction. The tensioning cable (70) attaches via a hook (73) to the central ring (45) attached to the stretch bands (40) on the frame (5).

In a preferred embodiment of the invention, a spring scale (71) is provided along the tensioning cable (70) between the harness (50) and the stretch bands (40). Optionally, the spring scale (71) can be made removable by providing a second hook (74) or other fastening means on the tensioning cable (70) near the point where it attaches to the harness ring (65), so that the hook (73) at the end of the tensioning cable (70) can be connected directly to the ring (45) if the spring scale is not desired, or if it is, the second hook (74) can be connected to one end of the scale (71) and the other end of the scale, or a short cable (77) attached to the other end of the scale, would then hook to the ring (45).

The spring scale enables the user (92) to know how much traction pull-weight he or she is applying to the lower spine. A "spotter" or assistant may be needed to read the traction weight scale if there is any chance the user (92) is exceeding the maximum allowed pull-weight.

To overcome the need for an assistant, the spring scale (71) may be replaced with an electronic scale with a remote display (72). The remote display (72) is preferably located near the top (15) of the frame (5) so the person using the traction device can read it. Alternatively, the simple spring scale (71) can be replaced with an electronic "talking scale" that periodically (i.e., approximately every 30 seconds) reads the amount of traction force being applied and announces the reading via digital voice technology. These remote-reading electronic scales can receive the force measurements from force sensors directly replacing the spring scale (71) shown in FIG. 3, or could read information from sensors at the attachment points of the stretch bands (40) or handle ropes (30).

A body support (95) is used to keep the user (92) comfortable. A preferable form for the body support (95) is an inflatable pad, such as a sleeping or exercise mattress with approximate dimensions of 72" long×25" wide×2" thick. A specific example of an inflatable mattress available for use in the traction device is a Therm-a-rests® (Camprest™ or Basecamp™ model, 72"×25"×2") self-inflating sleeping pad made by Cascade Designs, Inc., Seattle, Wash. When using the traction device, the user (92) lies atop the body support (95), which preferably lies atop the frame (5). The purpose of the body support (95) is to provide a comfortable surface for the user (92) to lie upon and, most importantly, to facilitate the sliding of the user's prone body, both forward (to increase traction force) and rearward (to decrease traction force). Optionally, a face/head support pillow (not shown) is used to help the user (92) keep his/her head vertical and comfortable.

Pieces of Styrofoam, at least 1½" thick are alternatively used as a body support (95). These pieces of Styrofoam are cut to fit inside the frame (5) to make a flat, level surface. This alternative is less portable and less comfortable than the inflatable pad described above.

In a preferred embodiment of the invention, weights (100) are used to hold the bottom (35) of the frame (5) down while the traction device is in use. The weights (100) are preferably "dumbbell" weights, but any type of weight is usable in the device. The weights (100) are placed one on each corner of the bottom (35) of the frame (5) to hold the frame (5) down during periods of heavy pulling. The preferred weights for the weights (100) are approximately 10 lbs. each for small people, 20 lbs. each for larger people. The weights (100) are optional, as the traction device can be used without them in the lower traction pull-weight ranges. While it is possible to use the traction device without weights (100) to hold down the bottom (35) of the frame (5), not using the weights (100) restricts the user (92) to the lower range of pull-weights.

The device is usable in the convenience of the user's home or office, or wherever the treatment is desired, rather than having to go to a clinic. The traction device also preferably utilizes a portable frame as a component to achieve the traction. The entire system weighs approximately 20 lbs. and optionally includes a carry bag. The carry bag is preferably approximately 36" long. The bag is preferably a zipper-closed, nylon carry bag that the entire device/system fits into for convenient transportation.

The traction device does not work as well if the user is so obese that he or she cannot make her/himself slide on the pad by pulling the handles.

A method of using the traction device is described below. First, the user (92) puts on the harness (50), attaches the sliding ring (65) to the tensioning cable (70), which is subsequently connected by hook (73) to the central ring (45) at the bottom (35) of the frame (5), and lies face-down. By lying face down, the user (92) is in one of the most relaxing and comfortable positions. When an inflatable pad is used as the body support (95), the user (92) is also very comfortable, and does not notice the frame cross-supports (10) beneath them.

Then, the user (92) grasps the grips (25) on the handles (20) and pulls himself slowly forward, sliding his/her body forward on the body support (95). By sliding forward on the body support (95), tension is put on the tensioning cable (70). The tensioning cable (70) causes the stretch bands (40) to stretch, resulting in a constant pull on the harness (50). The amount of pull exerted by the stretch bands (40) increases as they become more stretched out.

The user (92) instantly and easily changes the amount of traction he or she is getting by sliding herself forward or backward on the body support (95). The harder the user (92) pulls, the further he or she slides forward and the more the traction pull-weight is increased. When the user (92) has achieved the desired level of traction weight, he or she simply stops pulling, relaxes their lower back and begins enjoying soothing traction. The user (92) can almost completely relax their arms and let the stretch bands (40) do the work of pulling. The average person can relax his/her arms completely without sliding back even when 40–50 pounds of traction are being applied. At higher ranges, the user (92) has to continue to pull gently against the frame handles (20) to keep from sliding back. Normal arm strength in both arms is all that is required to apply traction. The desired level of traction weight is preferably measured using a spring scale (71), which an assistant or spotter can read for the user (92).

To be beneficial, a session of traction should begin with a very light pull-weight, for example approximately 20 pounds on the scale (71). The pull-weight is then gradually increased a few pounds at a time until, by the end of the session, the user (92) is at his/her optimum maximum for that session. The maximum is preferably determined by the user's physician prior to use. It is likely that the optimum maximum is much higher than the user (92) ever had with traditional, clinical traction. The user (92) is in complete control of the amount of traction being supplied at all times.

The user (92) should always follow a physician's advice as to how frequently he or she should use the traction device, and how long each session should last. Generally, no more than 30 minutes per day is needed to give a user (92) the maximum benefits of the traction. The amount of traction being applied should never lead to discomfort during the traction session.

The user easily varies the amount of traction pull-weight he or she applies with the traction device, where most other forms of traction are either "on" or "off." Easing into traction and slowly increasing the applied traction pull-weight over the session is much better than the "on/off" method.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A traction device for self-applying traction force to a user's body, comprising:
    a) an anchor system;
    b) at least one hand grip attached to the anchor system at a location which is above a head of the user during use;
    c) at least one resilient band attached to the anchor system at a location which is below the user's feet during use;
    d) a harness capable of attachment to the waist of the user;
    e) a tensioning cable connecting the harness to the resilient band,
    such that when the user grips the hand grip and pulls on the hand grip, causing the user's body in the harness to move, the motion causes the tension cable to stretch the resilient band, exerting a traction force to the user's body.

2. The traction device of claim 1 further comprising a body support such that said body support facilitates a sliding motion of a body of a user both forward and rearward during a traction session.

3. The traction device of claim 2 wherein said body support is a plurality of Styrofoam pieces cut to fit inside a frame and create a surface which is flat and level.

4. The traction device of claim 2 wherein said body support is an inflatable pad.

5. The traction device of claim 1 wherein said tensioning cable is made of a material selected from a group comprised of rope, wire, chain or webbing.

6. The traction device of claim 1 further comprising a force-measuring device for reading an amount of pull-weight a user is applying to a lower spine during a traction session.

7. The traction device of claim 6 wherein the force-measuring device is a spring scale.

8. The traction device of claim 6 wherein said force-measuring device is an electronic scale.

9. The traction device of claim 8 wherein said electronic scale further comprises a remote display.

10. The traction device of claim 9 wherein said remote display is located in plain view of a user during a traction session.

11. The traction device of claim 9 wherein said electronic scale further comprises a voice synthesizer for announcing the force being measured.

12. The traction device of claim 6, in which the force-measuring device is in the tensioning cable.

13. The traction device of claim 1 wherein said anchoring system comprises at least one wall.

14. The traction device of claim 1 wherein said anchoring system is a rigid frame, sized such that the user is enclosed in the frame during use.

15. The traction device of claim 14 wherein said frame further comprises a top end, a bottom end, and first and second sides and at least two cross supports, such that each cross support is parallel to said top end and said bottom end, and is perpendicular to and connect said first and said second sides.

16. The traction device of claim 14 wherein said frame is comprised of a material selected from the group consisting of plastic tubing; aluminum; steel; and wood.

17. The traction device of claim 14 wherein said frame has a substantially rectangular shape.

18. The traction device of claim 14 wherein said frame is approximately 8 feet long and 3 feet wide.

19. The traction device of claim 14 further comprising at least one weight such that said weight holds down said frame during a traction session.

20. The traction device of claim 1 further comprising a support pillow for a head of said user.

21. The traction device of claim 1 wherein the handgrip comprises at least one handle comprising a grip and a rope connecting the grip to the anchoring system.

22. The traction system of claim 21 in which the length of said rope is variable.

23. The traction device of claim 1 wherein the resilient band is made of a material selected from the group consisting of an elastic material and a spring.

24. The traction device of claim 1, in which there are a plurality of resilient bands, connected in parallel.

25. The traction device of claim 24 wherein said harness is comprised of a nylon strapping material.

26. The traction device of claim 24 wherein said front waistband section and said rear waistband section are connectable by a buckle on each side of said harness.

27. The traction device of claim 24 wherein the waistband section is fastened around a waist of a user just above the hips of said user.

28. The traction device of claim 1, in which the harness comprises:

i) a waistband having a front section and a rear section;

ii) at least two downstraps attached to said waistband such that each downstrap is connected to both said front section section and said rear section; and iii) a ring, wherein each of said downstraps pass through said ring, and said ring is connected to said tensioning cable.

* * * * *